United States Patent
Schmitz et al.

[11] Patent Number: 5,935,506
[45] Date of Patent: Aug. 10, 1999

[54] METHOD FOR THE MANUFACTURE OF INTRALUMINAL STENTS OF BIORESORBABLE POLYMERIC MATERIAL

[75] Inventors: Klaus-Peter Schmitz; Detlef Behrend, both of Warnemünde, Germany

[73] Assignee: Biotronik Meβ- und Therapiegeräte GmbH & Co. Ingenieurbüro Berlin, Berlin, Germany

[21] Appl. No.: 08/733,172

[22] Filed: Oct. 17, 1996

[30] Foreign Application Priority Data

Oct. 24, 1995 [DE] Germany .................... 195 39 449

[51] Int. Cl.⁶ .................. B29C 33/40; B28B 1/38; A61F 2/06
[52] U.S. Cl. .................. 264/400; 264/221; 264/238; 264/255; 264/305; 264/306; 264/310; 264/313; 264/317; 604/265; 623/900; 623/901
[58] Field of Search .................. 264/255, 305, 264/306, 310, 313, 317, 221, 338, 400; 623/900, 901; 604/265

[56] References Cited

U.S. PATENT DOCUMENTS

| | | | |
|---|---|---|---|
| 4,123,582 | 10/1978 | Musyt | 428/335 |
| 4,506,672 | 3/1985 | Bichon | 128/335.5 |
| 4,603,152 | 7/1986 | Laurin et al. | 604/265 |
| 4,677,143 | 6/1987 | Laurin et al. | 523/122 |
| 4,731,073 | 3/1988 | Robinson | 623/1 |
| 4,777,002 | 10/1988 | Putz | 264/226 |
| 4,882,176 | 11/1989 | Koyama et al. | 426/5 |
| 4,955,899 | 9/1990 | Della Corna et al. | 623/1 |
| 5,066,772 | 11/1991 | Tang et al. | 528/354 |
| 5,354,329 | 10/1994 | Whalen | 623/1 |
| 5,449,382 | 9/1995 | Dayton | 623/1 |
| 5,605,696 | 2/1997 | Eury et al. | 424/423 |
| 5,679,400 | 10/1997 | Tuch | 427/2.14 |

FOREIGN PATENT DOCUMENTS

| | | |
|---|---|---|
| 0 466 105 | 1/1992 | European Pat. Off. . |
| 0 578 998 | 1/1994 | European Pat. Off. . |
| 43 36 209 | 3/1995 | Germany . |
| 43 34 272 | 4/1995 | Germany . |

OTHER PUBLICATIONS

Agrawal, C.M. et al., "Evaluation of poly(L–lactic acid) as a material for intravascular polymeric stents.", Biomaterials, vol. 13, no. 3, pp. 176–182 (1992).

Rajasubramanian, Ganesh et al., "Fabrication of resorable microporous intravascular stents for gene therapy.", Asaio Journal, pp. M584–M589 (1994).

*Primary Examiner*—Catherine Timm
*Assistant Examiner*—Suzanne E. Mason
*Attorney, Agent, or Firm*—Browdy and Neimark

[57] ABSTRACT

A method for the manufacture of intravascular stents of bioresorbable material comprises the following steps:

preparing a viscous solution of poly-β-hydroxybutanoic acid as a bioresorbable polymeric material in a solvent, successively coating a male mold core with layers of the polymer solution in several steps by precipitation of the polymeric material by the solvent being evaporated and by the layer previously precipitated being dissolved at least partially for a homogeneous stent blank to build up, drawing the stent blank off the male mold core, and subsequently treating the stent blank to finish the shaping of the stent.

20 Claims, 1 Drawing Sheet

METHOD FOR THE MANUFACTURE OF INTRALUMINAL STENTS OF BIORESORBABLE POLYMERIC MATERIAL

BACKGROUND OF THE INVENTION

1. Field of the Invention

The invention relates to a method for the manufacture of intraluminal stents of bioresorbable polymeric material.

2. Background Art

As regards the technological background of the invention, it has to be explained that for the manufacure for instance of implantable intravascular stents—i.e. of angioplastic vessel wall supports to be used in cardiac surgery—conventional methods of plastics technology are known and used, which are based on the processing of thermoplastic polymeric materials. Stents, which are small tubes of some few millimeters of diameter and few centimeters of length, are produced by extrusion or injection-molding. In this connection, reference must be made to the essay, "Evaluation of poly (L-lactic acid) as a material for intravascular polymeric stents", by Agrawal et al., in Biomaterials 1992, vol. 13, no. 3, pages 176 to 187, mentioning the use of poly (L-lactic acid) monofilaments for the manufacture of intravascular polymeric stents. These monofilaments are extruded and drawn to different draw ratios. Monofilaments thus treated are then used for the construction of stents.

The disadvantage of the known methods resides in that they may lead to the polymeric material being thermally damaged during the extrusion process or injection-molding. The high crystallinity of the materials used can make thermoplastic transformation processes very difficult.

The essay, "Fabrication of Resorbable Microporous Intravascular Stents for Gene Therapy Applications", by Rajasubramanian et al, ASAIO Journal 1994, pages M584 to M589, teaches to manufacture resorbable, microporous stents from a mixture of poly-L-lactic acid (PLLA) and poly-E-caprolacton (PCL), spiral as well as tubular stent constructions being produced by dissolution of this polymeric mixture in an organic solvent (1,4-dioxane) and by subsequent flotation of the polymer. During this flotation, the polymer solution is sprayed on a water surface flowing steadily, the solvent thus dispersing in the water and evaporating from the surface. This helps form a polymer precipitation floating as a film on the water surface and being taken up, at a suitable place, by a mandrel, on which will form a multi-layer coating of the partially cured polymer. After completion of the coating, the mandrel is placed into a vacuum furnace for the curing process to be completed over a period of 24 hours at 45° C. Then the mandrel comprising the polymer coating is soaked in a 50 per cent ethanol solution for the polymer coating to swell, after which it can be removed from the mandrel.

The known method poses problems in as much as the flotation of the polymer film and the "take-up" of the polymer film by the mandrel is very difficult and susceptible to process fluctuations. Moreover, there is the need of complicated subsequent treatment of the stent blanks thus produced. Another disadvantage of this method resides in that no isotropic structure within the stent can be attained by this manufacturing technology. This is of disadvantage for any steady resorption in vivo and negatively affects the mechanical properties of the stent.

SUMMARY OF THE INVENTION

It is the object of the invention to specify a method for the manufacture of intraluminal stents of bioresorbable polymeric material, leading to stents of good bioresorption properties accompanied with simplified process technology.

This object is attained by the operational steps according to the invention, which consist in:
- preparing a viscous solution of poly-β-hydroxybutanoic acid as a bioresorbable polymeric material in a solvent,
- successively coating a male mold core with layers of the viscous polymer solution in several steps by precipitation of the polymeric material by the solvent being evaporated and by the layer previously precipitated being dissolved at least partially for a homogeneous stent blank to build up,
- drawing the stent blank off the male mold core, and
- subsequently treating the stent blank to finish the shaping of the stent.

By advantage, the method according to the invention no longer proceeds from a polymeric mixture, but from a uniform polymeric material in the form of poly-β-hydroxybutanoic acid. As compared to prior art, one can do without the complicated flotation for precipitation of the polymer film.

Rather, in accordance with the preferred embodiments of the method according to the invention, the proceeding consists in dipping the male mold core several times into the polymer solution and then removing the core from the solution or, respectively, in pouring the polymer solution over the core in several successive operations. In terms of process technology, both alternatives are by far easier to master and less prone to process fluctuations than the known prior art method described above.

Furthermore, stents of poly-β-hydroxybutanoic acid have proved to be biologically compatible and well bioresorbable. In this regard, the use of the stents according to the invention will not be restricted to intravascular stents, it being possible just as well to produce vessel wall supports for gastro or urologic surgery.

Preferably, the rotation of the male mold core during the build-up of the stent blank improves the latter's homogeneity by making the build-up operation more uniform.

According to a further preferred embodiment of the invention, preparing the polymer solution consists in dissolving in chloroform poly-β-hydroxybutanoic acid as a powder in a percentage of 2 to 3% by weight referred to the total quantity of the solution. This is done by agitating preferably at temperatures ranging between 50 and 70° C.

It is further provided to add a biocompatible plasticizer to the polymer solution, the mechanical properties of the stent thus being adjusted correspondingly. Ethyl citrate of a concentration of 5 to 50% by weight referred to the total quantity of the solution is provided as a preferred plasticizer.

To improve the removability the stent blanks from the mold, a biocompatible release agent is coated on the male mold core prior to its being coated with the polymer solution. This release agent is insoluble in the solvent of the polymer solution, while being soluble in any other solvent. In particular a concentrated sugar solution (glucose or glucosid solutions) is used as a release agent, which is dissolved by distilled water prior to the removal of the stent blank from the male mold core. Since such sugar solutions are excellently soluble in distilled water, however insoluble in chloroform, the coating produced thereby of the male mold core is a good basis for the deposition of the viscous polymer solution. After the stent blank has been finished, the coating is very quickly dissolved by the distilled water, this producing an annular gap between the male mold core and the sensitive stent blank, as a result of which the sensitive blank rests virtually loose on the mold core and can simply be drawn off.

Further preferred embodiments of the invention characterize measures by which to improve the product properties of the stent thus produced. For instance, for the continuous release of pharmaceutical anticoagulants or cell-proliferation-inhibiting agents during bioresorption of the stent, these agents can be incorporated into the volume of the stent by being added to the polymer solution. The distribution of the pharmaceutical agents can be homogeneous throughout the stent volume or in layers. In the latter case, the individual dipping or pouring processes work with different polymer solutions (with or without the addition of pharmaceutical agents). By analogy, silver or silver alloys can be added to the polymer solution, which are incorporated homogeneously or in layers into the stent volume to work as an X-ray contrast medium and/or inflammation-inhibiting agent.

A step of filtering the polymer solution serves to homogenize and clean the polymer solution.

Laser-beam or water-jet cutting has established as an advantageous mechanical method of subsequently treating the stent blanks.

An intravascular stent of bioresorbable polymeric material produced by the method according to the invention is made from a basic material, namely poly-β-hydroxybutanoic acid.

Further features, details and advantages of the invention will become apparent from the ensuing description of an exemplary embodiment of the method according to the invention, taken in conjunction with the drawing.

DESCRIPTION OF THE PREFERRED EMBODIMENT

A method according to the invention for the manufacture of a resorbable intravascular stent is explained in detail in the following, taken in conjunction with FIGS. 1 and 2.

In the present exemplary embodiment, three polymer solutions are prepared, the type and quantity of the polymer and solvent of which are identical. To this end, 4 g pulverulent poly-β-hydroxybutanoic acid are dissolved in 100 ml chloroform as an organic solvent by stirring by means of a magnetic stirrer at a temperature of 56° C. Further, a biocompatible plasticizer, namely ethyl citrate, is added to the solution by stirring in a concentration of 5 to 50% by weight for the adjustment of the desired mechanical properties of the stent.

A pharmaceutical anticoagulant is added to the first of the three solutions. Silver particles serving as an X-ray contrast medium in the finished stent are added to the third of the three solutions. The solutions are then filtered through a frit preferably of the type 3g3.

Figure 1:
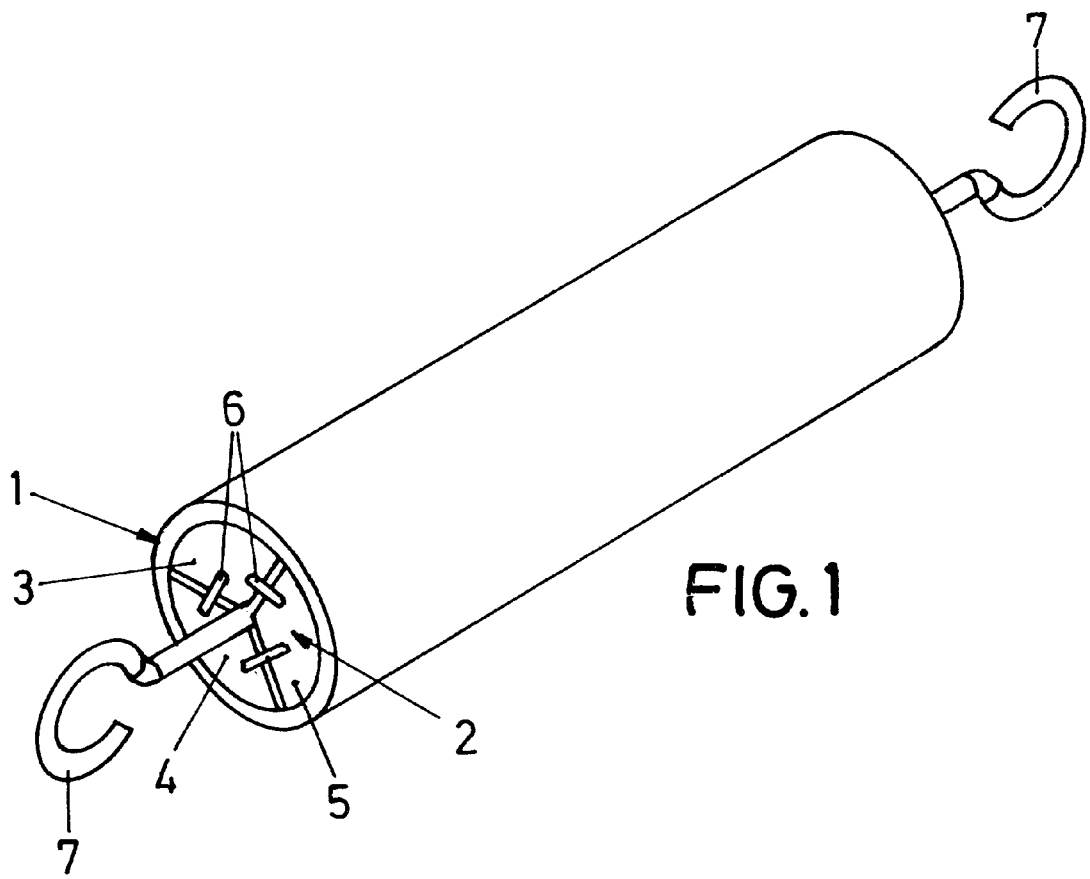
FIG. 1 is a diagrammatic, perspective view of a stent built up on a male mold core.
Figure 2:
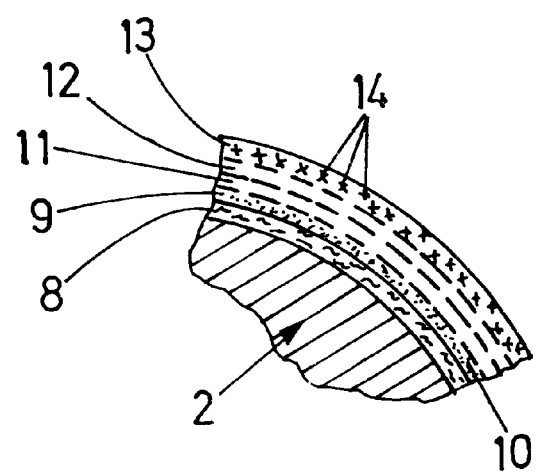
FIG. 2 is a cut of a cross-section, on an enlarged scale, through the stent blank resting on the mold core according to FIG. 1.

A so-called male mold core 2 serves for forming the stent blank 1, as seen in FIG. 1 and part of it in FIG. 2, the mold core 2 essentially being a cylinder piece of several centimeters of length and some few millimeters of diameter. As seen in FIG. 1, the male mold core 2 is composed of three elements 3, 4, 5 sector-pattern in cross-section, which are held together by wedging elements 6. The front ends of the male mold core 2 are provided with fixing eyelets 7, by means of which to handle the male mold core 2. The material used for the male mold core 2 is a non-adhesive material such as polytetrafluoroethylene.

As roughly outlined in FIG. 2, the male mold core 2, prior to the build-up of the stent blank 1, is provided with a biocompatible release coating 8 of a concentrated glucosid solution which is not soluble in chloroform, but excellently soluble in distilled water.

For the successive build-up in layers of the stent blank 1, the male mold core 2 thus prepared is dipped into the first solution prepared, from which it is again removed after a short while. A first layer 9 of this polymer solution adheres to the release coating 8. During a short period of rotation of the male mold core 2, the poly-β-hydroxybutanoic acid is precipitated by evaporation of the chloroform. As outlined by dots in FIG. 2, the pharmaceutical anticoagulant 10 is homogeneously distributed in this first layer 9.

Then the mold core 2 is dipped into the second polymer solution, in which neither anticoagulants nor silver particles are available. After a short while, the male mold core 2 is again removed from this solution, the second layer 11 adhering to the first layer 9. By rotation of the mold core 2, again precipitation of the poly-β-hydroxybutanoic acid takes place, accompanied with the evaporation of chloroform. The first layer 9 is at least partially dissolved, which helps produce an intimate molecular linkage towards the first layer 9 so that the stent blank 1 is homogeneous as far as its polymer structure is concerned.

The operation is repeated for the third layer 12 to form.

For the formation of the fourth layer 13, which constitutes the outer layer of the stent blank 1, the mold core 2 is dipped into the third solution in which silver particles are distributed. After removal of the mold core 2 from this solution, this fourth layer 13 adheres to the third layer 12, silver particles 14 being homogeneously distributed in this fourth layer 13—as outlined by crosses in FIG. 2. As discussed, these silver particles serve as an X-ray contrast medium.

The mold core with the stent blank 1 built up on it is then dried by rotation for a period of 2 to 10 minutes, all the layers 9, 11, 12, 13 polymerizing perfectly, entering into an intimate molecular linkage within themselves as well as among each other so that, as far as the polymer structure is concerned, no inhomogeneities—i.e. no layer structure—will be found in the polymerized, finished stent blank 1. Only the pharmaceutical anticoagulants 10 are discernible towards the inside and the silver particles 14 towards the outside.

For the stent blank 1 to be removed from the male mold core 2, the entire arrangement is dipped into distilled water, which will dissolve the release coating 8. As a result, the stent blank 1 rests loose on the male mold core 2 and can be drawn off virtually resistancelessly.

By laser-beam cutting the stent bank 1 drawn off is then cut to its desired length of 3 cm as a rule. Its outer diameter amounts to approximately 3 mm, its wall thickness to some tenths of a millimeter. In this regard, it is self-evident that the illustration of FIG. 2 is of purely diagrammatic nature and that the thicknesses of the layers shown are strongly exaggerated.

When a stent of this type is implanted, its position in a coronary vessel can be verified very well radiographically, owing to the silver particles 14 in the outer layer. The pharmaceutical anticoagulants 10 of the inward, first layer 9 improve the biocompatibility of the implanted stent. During the bioresorption of the stent, they are continuously released, providing for a long-term effect.

Finally attention is drawn to the fact that, instead of being disposed in layers, the pharmaceutical anticoagulants 10 and the silver particles 14 can be incorporated to be homogeneously spread in the volume of the stent blank. In this case, only a single polymer solution is used, containing also the pharmaceutical anticoagulants and the silver particles.

What is claimed is:

1. A method for the manufacture of intravascular stents of bioresorbable polymeric material, comprising the following steps:

preparing a viscous polymer solution of poly-β-hydroxybutanoic acid as a bioresorbable polymeric material in a solvent, successively coating a surface of a male mold core (2) with layers of the polymer solution in several steps by precipitation of the polymeric material by the solvent being evaporated and by the layer previously precipitated being dissolved at least partially for a homogeneous stent blank (1) to build up, drawing the stent blank (1) off the male mold core (2), and subsequently treating the stent blank (1) to finish the shaping of the stent.

2. A method according to claim 1, wherein for successively coating the male mold core (2) with layers of the polymer solution, the male mold core (2) is alternatively dipped for several times into the polymer solution and removed from the latter for the solvent to evaporate from the layer (9, 11, 12, 13) of polymer solution depositing.

3. A method according to claim 1, wherein for successively coating the male mold core (2) with layers of the polymer solution, the latter is poured over the male mold core (2) in several successive operations, the previously adhering layer (9, 11, 12, 13) of polymer solution, between each pouring operation, being at least partially dissolved by the subsequent layer (11, 12, 13) of polymer solution and the polymeric material being precipitated by evaporation of the solvent.

4. A method according to claim 1, wherein the male mold core (2) is rotated during the build-up of the stent blank (1).

5. A method according to claim 1, wherein preparing the polymer solution consists in dissolving in chloroform poly-β-hydroxybutanoic acid as a powder in a percentage of 2 to 3% by weight referred to the total quantity of solution.

6. A method according to claim 5, wherein dissolving takes place by stirring at temperatures ranging between 50 and 70° C.

7. A method according to claim 1, wherein for adjustment of the mechanical properties of the stent, a biocompatible plasticizer of a concentration of 5 to 50% by weight is added to the polymer solution.

8. A method for the manufacture of intravascular stents of bioresorbable polymeric material, comprising:

preparing a viscous chloroform solution of poly-β-hydroxy-butanoic acid as a bioresorbable polymeric material, applying the chloroform solution of poly-β-hydroxy-butanoic acid directly to a surface of the male mold core (2), and successively coating with additional layers of the solution by precipitation of the polymeric material by evaporation of the chloroform and by the layer previously precipitated being dissolved at least partially for a homogeneous stent blank (1) to build up on said male mold surface, removing the stent blank (1) from the male mold core (2), and subsequently finishing the shaping of the stent;

wherein prior to being coated with the solution, the male mold core (2) is coated with a biocompatible release agent (8), which is insoluble in chloroform, but soluble in other solvents.

9. A method according to claim 8, wherein the release agent used is a concentrated sugar solution, which is dissolved by distilled water before the stent blank (1) is drawn off the male mold core (2).

10. A method according to claim 1, wherein at least one of a pharmaceutical anticoagulant and a cell-proliferation-inhibiting agent (10) is added to the polymer solution.

11. A method for the manufacture of intravascular stents of bioresorbable polymeric material, comprising:

preparing a viscous solution of poly-β-hydroxy-butanoic acid as a bioresorbable polymeric material in a solvent, successively coating a male mold core (2) with layers of the polymeric material in several steps by precipitation of the polymeric material by evaporation of the solvent and by the layer previously precipitated being dissolved at least partially for a homogeneous stent blank (1) to build up, removing the stent blank (1) from the male mold core (2), and subsequently finishing the shaping of the stent;

wherein at least one of a pharmaceutical anticoagulant and a cell-proliferation-inhibiting agent (10) is added to the solution, and is incorporated in the volume of the stent homogeneously for continuous release during bioresorption of the stent.

12. A method for the manufacture of intravascular stents of bioresorbable polymeric material, comprising:

preparing a viscous solution of poly-β-hydroxy-butanoic acid as a bioresorbable polymeric material in a solvent, successively coating a male mold core (2) with layers of the polymeric material in several steps by precipitation of the polymeric material by the evaporation of solvent and by the layer previously precipitated being dissolved at least partially for a homogeneous stent blank (1) to build up, removing the stent blank (1) from the male mold core (2), and subsequently finishing the shaping of the stent;

wherein at least one of a pharmaceutical anticoagulant and a cell-proliferation-inhibiting agent (10) is added to the solution, and is spread in one or several layers (9) for continuous release during bioresorption of the stent.

13. A method for the manufacture of intravascular stents of bioresorbable polymeric material, comprising:

preparing a viscous solution of poly-β-hydroxy-butanoic acid as a bioresorbable polymeric material in a solvent, successively coating a male mold core (2) with layers of the polymeric material in several steps by precipitation of the polymeric material by the evaporation of solvent and by the layer previously precipitated being dissolved at least partially for a homogeneous stent blank (1) to build up, and wherein particles (14) of at least one of silver and silver alloys are added to the solution for being incorporated as an X-ray contrast medium and inflammation-inhibiting agent into the volume of the stent, removing the stent blank (1) from the male mold core (2), and subsequently finishing the shaping of the stent.

14. A method according to claim 1, wherein prior to the coating of the male mold core (2) with the polymer solution, the latter is filtered through a frit.

15. A method according to claim 1, wherein the stent blank (1) is subsequently treated by at least one of laser-beam cutting and water-jet cutting.

16. A method according to claim 7, wherein said biocompatible plasticizer is ethyl citrate.

17. A method according to claim 9, wherein ethyl citrate of a concentration of 5–50% by weight is added to the solution.

18. A method according to claim 8, wherein the release agent used is a concentrated glucosid solution.

19. A method according to claim 1, wherein said successively coating comprises applying a first coating of said polymer solution containing a biocompatible plasticizer and a pharmaceutical anticoagulant to form a first layer; after evaporation of solvent from said first layer, applying thereto a second solution of said polymer containing a biocompatible plasticizer to form a second layer integral with said first layer; after evaporation of solvent from said second layer, applying a third layer of said polymer solution containing a biocompatible plasticizer, said third layer optionally also containing particles of an x-ray contrast medium, thereby providing a third layer integral with said second layer; and, after evaporating solvent from said third layer, optionally applying a fourth layer of said polymer solution optionally containing particles of an x-ray contrast medium therein.

20. A method according to claim 19, comprising only three or four of said applications of coatings.

* * * * *